United States Patent [19]
Iijima

[11] Patent Number: 5,975,698
[45] Date of Patent: Nov. 2, 1999

[54] OPHTHALMIC INSTRUMENT

[75] Inventor: Hiroshi Iijima, Tokyo, Japan

[73] Assignee: Kabushiki Kaisha Topcon, Tokyo, Japan

[21] Appl. No.: 09/168,086

[22] Filed: Oct. 8, 1998

[30] Foreign Application Priority Data

Oct. 9, 1997 [JP] Japan .................................. 9-277563

[51] Int. Cl.⁶ ...................................................... A61B 3/14
[52] U.S. Cl. .......................................................... 351/208
[58] Field of Search .................................... 351/205, 206, 351/208, 209, 211, 212, 221, 246

[56] References Cited

U.S. PATENT DOCUMENTS 5,644,375  7/1997  Suzuki ..................................... 351/208
5,905,562  5/1999  Isogai et al. ............................. 351/208

Primary Examiner—George Manuel
Attorney, Agent, or Firm—Finnegan, Henderson, Farabow, Garrett & Dunner, L.L.P.

[57] ABSTRACT

Disclosed herein is an ophthalmic instrument comprising: an optical measuring section (101) for housing an optical system that measures characteristics of an object eye; an alignment detecting optical system (17') for optically detecting an offset quantity in alignment between the optical measuring section and the object eye; drive units (102 and 103) for moving the optical measuring section (101) vertically, laterally, and longitudinally on the basis of the offset quantity detected by the alignment detecting system (17'); and a control circuit (51) for transmitting a signal which instructs start of measurement to the optical measuring section (101) when the alignment detecting system detects that the object eye has been moved within a measurable area. Prior to the start of measurement the control circuit (51) continues to move the optical measuring section (101) for only a predetermined time so that the object eye (optical axis Oe of the object eye) is moved within a drive target area smaller than the measurable area and also included in the measurable area.

4 Claims, 11 Drawing Sheets

OPHTHALMIC INSTRUMENT

BACKGROUND OF THE INVENTION

1. Field of the Invention

The present invention relates to an ophthalmic instrument equipped with an automatic alignment mechanism and also constructed so that measurement is automatically started when the alignment between the instrument main body and an object eye has been completed by the automatic alignment mechanism.

2. Description the Prior Art

Conventionally, an ophthalmic instrument is provided with an automatic alignment mechanism and an automatic measurement starting mechanism for simplifying the operations to them.

The automatic alignment mechanism has an alignment detecting optical system that optically detects an offset quantity Δ in alignment and a drive control unit, such as a pulse motor, which move the instrument main body based on the detection result in a direction in which the detected alignment offset quantity Δ is reduced. The automatic measurement starting mechanism is constructed so that when the measurement error due to the alignment offset quantity Δ has reduced to be negligible, the operation of the drive control unit is stopped and also a measurement start signal is output to the optical measuring section to make the instrument main body start an operation necessary for measurement (e.g., jetting of an air pulse for cornea deformation in a non-contact type tonometer). In other words, assuming that the maximum value of the offset quantity between the optical axis O1 of the optical measuring system and the optical axis Oe of an object eye, which is allowable in obtaining reliable measured values, is ΔO, the measurement start signal is output when the actual offset quantity Δ is less than the allowable limit ΔO.

However, the aforementioned conventional ophthalmic instrument outputs the measurement start signal even when the alignment offset quantity Δ is slightly less than the allowable limit ΔO (e.g., as shown in FIG. 12, even when the optical axis Oe of the object eye is located near the inside of the boundary of a circle with a radius of "ao" representing the allowable limit).

For this reason, in an ophthalmic instrument that has some time lag between the reception of the measurement start signal and the start of an operation necessary for measurement, there are cases where the optical axis Oe of the object eye will be moved from the inside vicinity to the outside of the aforementioned circle with a radius of "ao" during this time lag. For this reason, there is a problem that the measured values will lack reliability.

SUMMARY OF THE INVENTION

It is an object of the present invention to provide an ophthalmic instrument that is capable of enhancing the reliability of measured values.

To achieve this object, there is provided an ophthalmic instrument comprising: an optical measuring section for housing an optical system that measures characteristics of an object eye; an alignment detecting optical system for optically detecting an offset quantity in alignment between the optical measuring section and the object eye; drive means for moving the optical measuring section vertically, laterally, and longitudinally on the basis of the offset quantity detected by the alignment detecting optical system; and measurement start instructing means for transmitting a signal that instructs start of measurement to the optical measuring section when the alignment detecting system detects that the object eye has been moved within a measurable area, wherein the drive means, prior to the operation of the measurement start instructing means, continues to move the optical measuring section for only a predetermined time so that the object eye is moved within a drive target area smaller than the measurable area and also included in the measurable area.

BRIEF DESCRIPTION OF THE DRAWINGS

The above and other objects and advantages will become apparent from the following detailed description when read in conjunction with the accompanying drawings wherein.

DETAILED DESCRIPTION OF THE PREFERRED EMBODIMENTS

Embodiments of an ophthalmic instrument according to the present invention will hereinafter be described in detail based on the drawings.

FIRST EMBODIMENT

<OPTICAL SYSTEM>

Figure 1A:
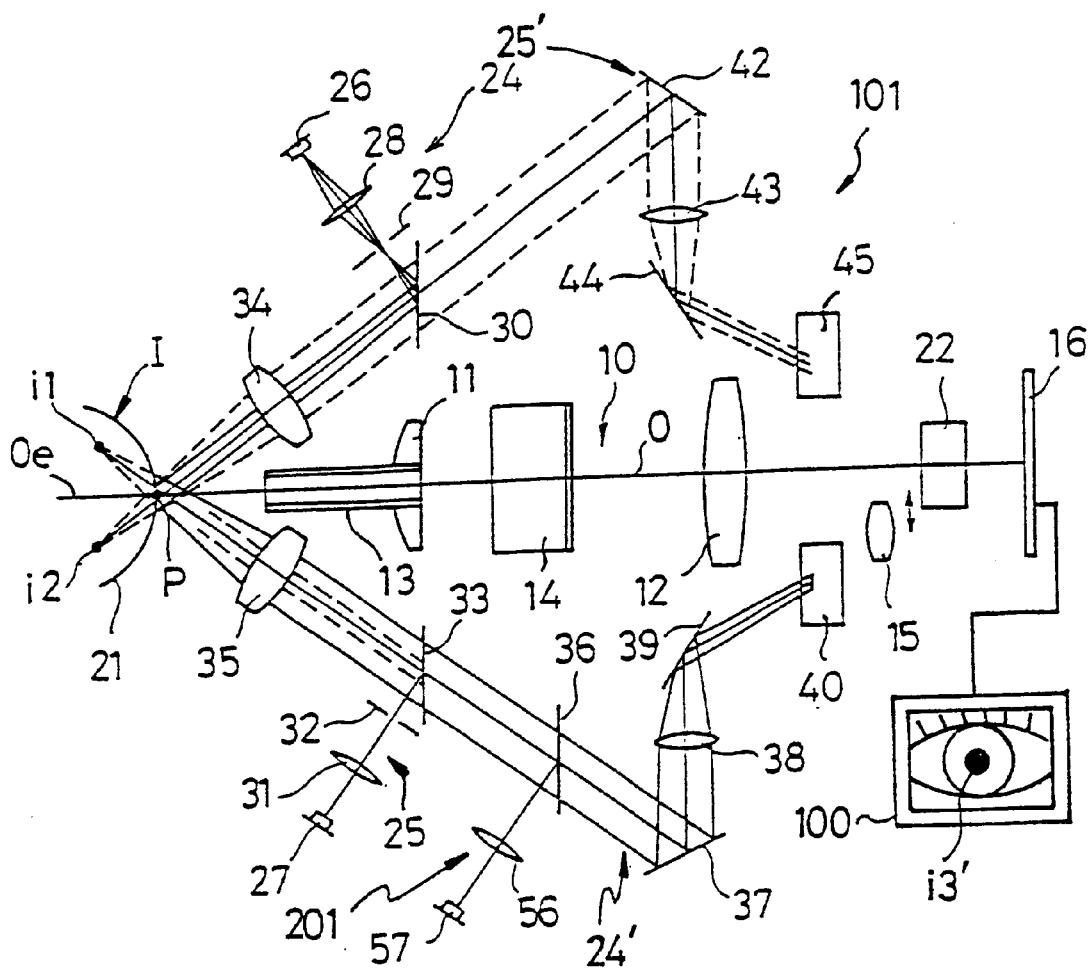
FIG. 1(A) is a plan view showing the optical system of an ophthalmic instrument according to a first embodiment of the present invention.

FIGS. 1(A) and 1(B) show an optical system of a non-contact type tonometer to which the present invention is applied. FIGS. 1(A) and 1(B) show a plan view of the optical system and a side view of the optical system, respectively. Assume in FIG. 1(A) that the vertical direction and the lateral direction (perpendicular to paper surface) of the optical system are the X-direction and the Y-direction, respectively. Also, assume that the direction parallel to the optical axis O of the optical system is the Z-direction.

The optical system of the non-contact type tonometer is roughly constituted by a front eye portion observing optical system 10, an XY-alignment index light projecting optical system 17, an XY-alignment detecting optical system 17', Z-alignment index light projecting optical systems 24 and 25, Z-alignment index light receiving optical systems 24' and 25', and so on.

<FRONT EYE PORTION OBSERVING OPTICAL SYSTEM>

The front eye portion observing optical system 10 is equipped with an objective lens 11, a half mirror 14, an image forming lens 12, a correcting lens 15, a half mirror 22, and a charge coupled device (CCD) camera 16. With this arrangement, a light beam forming an image of a front eye portion is projected onto the CCD camera 16 through the objective lens 11, the half mirror 14, the image forming lens 12, the correcting lens 15, and the half mirror 22. The CCD camera 16 converts the received front eye portion image forming light beam to an image signal, thereby forming the front eye portion image on a monitor 100.

The correcting lens 15 is inserted into the optical axis O when the object eye I is farther than an appropriate distance and is removed from the optical axis O when the object eye I is at the appropriate distance or nearer than the appropriate distance. The insertion and removal of this correcting lens 15 are performed by a solenoid (not shown). Note that a spraying nozzle 13 is provided in the optical axis O of the objective lens 11 for jetting an air pulse for the measurement of intraocular tension to the object eye I .

<ALIGNMENT DETECTING OPTICAL SYSTEM>

The XY-alignment index light projecting optical system 17 is for projecting an index light onto the object eye I for detecting the alignment of an optical axis Oe of the object eye with the optical axis O of the front eye portion observing optical system 10. For this reason, the XY-alignment index light projecting optical system 17 is equipped with a light-emitting diode (LED) 18 used as a light source to emit an infrared light, a pinhole 19 for changing the light beam from this LED 18 to a light beam emitted from a point light source, a collimator lens 20 for changing the light beam from this pinhole 19 to a collimated light beam, the aforementioned half mirror 14, and so on. That is, the XY-alignment index light projecting optical system 17 is constructed so that a collimated light beam can be projected toward the cornea 21 of the object eye I through the interior hole of the spraying nozzle 13 and utilized as an alignment index light.

The XY-alignment detecting optical system 17' is for detecting the alignment state between the optical axis Oe of the object eye I and the optical axis O by making the alignment index light reflected at the cornela C be received by a light receiving element 23. For this reason, the XY-alignment detecting optical system 17' is equipped with the aforementioned half mirror 14, image forming lens 12, half mirror 22, light receiving element 23 capable of detecting a two-dimensional position, and CCD camera 16. With this arrangement, the alignment index light, reflected at the cornea C, is guided to the half mirror 22 through the interior hole of the spraying nozzle 13, image forming lens 12, etc. Then, the guided alignment index light is reflected at the half mirror 22 and projected onto the light receiving element 23, whereby an index image i3 is formed. Based on the position at which the index image i3 is formed, the alignment state between the instrument main body and the object eye I is detected.

A portion of the light not reflected at the half mirror 22 is projected on the CCD camera 16, whereby the index image i3 is also formed on the CCD camera 16. With this, the front eye portion image and an index image i3' are displayed on the monitor 100. Based on the positional relationship between these images, the tester can confirm the alignment stage with the naked eye. A reticle image, which is employed as a reference for alignment adjustment, is also electrically synthesized and displayed on the monitor 100

The Z-alignment index light projecting optical system 24 is equipped with an LED 26 for emitting an infrared light with a wavelength of 760 nm, a condenser lens 28, a pinhole 29, a dichroic mirror 30 for reflecting the infrared light with the wavelength of 760 nm and transmitting infrared light with a wavelength of 860 nm, and an objective lens 34 having itS focal point at the position of the pinhole 29. With this arrangement, a collimated light beam as an index for Z-alignment is projected from a right oblique direction toward the object eye I. As a result, a right index image i1 is formed on the object eye I. On the other hand, the Z-alignment index light projecting optical system 25 is equipped with an LED 27 for emitting an infrared light with a wavelength of 860 nm, a condenser lens 31, a pinhole 32, a dichroic mirror 33 for reflecting an infrared light with a wavelength of 860 nm and transmitting an infrared light with a wavelength of 760 nm, and an objective lens 35 having its focal point at the position of the pinhole 32. With this arrangement, a collimated light beam as an index for Z-alignment is projected from a left oblique direction toward the subjection eye I. As a result, a left index image i2 is formed on the object eye I. The right and left Z-alignment index light projecting optical systems 24 and 25 are symmetrically arranged with respect to the optical axis O of the objective lens 11 of the front eye portion observing system 10.

The Z-alignment index light receiving optical system 25' is equipped with the aforementioned objective lens 34, a mirror 42, a relay lens 43, a second mirror 44, a total reflecting mirror 45, and the aforementioned light receiving element 41. As clearly shown in FIG. 1(A), the Z-alignment index light receiving optical system 25' shares the objective lens 34 with the Z. alignment index light projecting optical system 24, and the Z-alignment index light projecting optical systems 24 and 25, as previously described, are symmetrically arranged with respect to the optical axis O of the objective lens 11 of the front eye portion observing optical system 10. For this reason, the index light beam from the Z-alignment index light projecting optical system 25 is reflected at the cornea 21 and reaches the total reflecting mirror 45 through the objective lens 34 and relay lens 43. As a result, the left index image i2 is again formed on the light receiving element 41.

The Z-alignment index light receiving optical system 24' is equipped with the aforementioned objective lens 35, the aforementioned dichroic mirror 33, a mirror 37, a relay lens 38, a mirror 39, and a total reflecting mirror 40. As clearly shown in FIG. 1(A), the Z-alignment index light receiving optical system 24' shares the objective lens 35 with the Z-alignment index light projecting optical system 25. For this reason, the index light beam from the Z-alignment index light projecting optical system 24 is reflected at the cornea 21 and reaches the total reflecting mirror 40 through the objective lens 35 and relay lens 38. As a result, the right index image i1 is again formed on the light receiving element 41.

When the distance from the cornea vertex P of the object eye I to the front end Q of the spraying nozzle 13 is within a normal operating distance, the index images i1 and i2 are formed on the light receiving element 41 so that they are wholly overlapped with each other, and in cases other than that, the index images i1 and i2 are separately formed on the light receiving element 41. Therefore, by detecting this overlapping wholly or not overlapping, it can be detected whether or not the operating distance, i.e., Z-alignment, has been appropriately performed. By changing the ON-OFF cycles of the LEDs 26 and 27 so that they differ from each other or changing the configurations of the pinholes 29 and 32 so that they differ from each other, it may be judged whether the operating distance is long or short. Note that the LEDs 26 and 27 are turned on and off by a control circuit (not shown).

Thus, in the first embodiment, as previously described, Z-alignment index light beams are projected from two symmetrically different directions, and the positions of the centers of gravity of the two index images on the light receiving element 41 are computed (i.e., averaged). From the computed positions of the centers of gravity, the positions of the index images are obtained. Therefore, even if XY-alignment is considerably offset, there is an advantage that the measurement error in the Z-alignment is reduced.

<CORNEA-DEFORMATION DETECTING OPTICAL SYSTEM>

A cornea-deformation detecting optical system 201 shares a portion of the optical system with the Z-alignment index light receiving optical system 24'. That is, the cornea-deformation detecting optical system 201 is equipped with the aforementioned objective lens 35, the aforementioned half mirror 36, a condenser lens 56, and a light receiving element 57, With this arrangement, the index light from the Z-alignment index light projecting optical system 24 is projected onto the light receiving element 57 through these optical elements, and also a temporal change in the quantity of the light received on the light receiving element 57, based on the air pulse jetted from the spraying nozzle 13 toward the cornea 21, is detected, whereby the intraocular tension in the object eye I is measured. That is, the Z-alignment index light projecting optical system 24 does not only serve as an optical system for projecting an index light for Z-alignment detection but also serves as an optical system for projecting a light beam for cornea deformation detection onto the object eye I.

<ARITHMETIC CONTROL SYSTEM AND DRIVE CONTROL UNIT>

The non-contact type tonometer of the embodiment is also equipped with an arithmetic control system for computing an alignment offset quantity on the basis of the output of the aforementioned alignment detecting optical system, and a drive control unit for driving and controlling the instrument main body on the basis of the computation result.

The arithmetic control system is equipped with a signal processing circuit 49, a signal processing circuit 50, and a control circuit 51 The signal processing circuit 49 is connected to the light receiving element 41 to receive an output of the light receiving element 41 at its input terminal, and has a function of detecting the positions of the centers of gravity of a pair of index images i1 and i2. On the other hand, the signal processing circuit 50 is connected to the light receiving element 23 to receive an output of the light receiving element 23 at its input terminal, and has a function of detecting the center of gravity of the index image i3.

The detection results of the signal processing circuits 49 and 50 are input to the control circuit 51. The control circuit 51 is constituted so as to compute both the center-to-center distance of the couple of the index images i1 and i2 and the position of the center of gravity of the index image i3.

The control circuit 51 has a function of computing both the offset quantity $\Delta$ between the optical axis O and the optical axis Oe of the object eye and the distance between the object eye cornea 21 and the instrument, from the position of the center of gravity of the index image i3 and the center-to-center distance of the couple of the index images i1 and i2. These computation results are output to a vertical drive unit 103 and a longitudinal-and-lateral drive unit 102. The vertical drive unit 103 and the longitudinal-and-lateral drive unit 102 have a function of moving the instrument main body vertically, laterally, and longitudinally on the basis of the input computation results to perform alignment adjustment.

The control circuit 51 also judges whether or not the offset quantity $\Delta$ has become equal to or less than a predetermined value $\Delta\bigcirc$. The reason why this judgment is performed is that when $\Delta \leqq \Delta\bigcirc$, a measurement error in an intraocular tension value caused by the offset quantity $\Delta$ itself is negligible and therefore measurement which can neglect the measurement error becomes possible. In the following description, an area where $\Delta \leqq \Delta\bigcirc$, will hereinafter be referred to as a "measurable area K".

Figure 11:
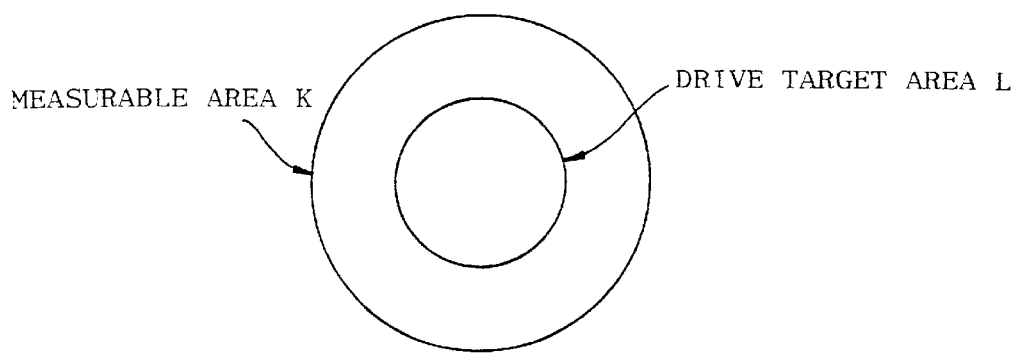
FIG. 11 is a conceptual diagram showing the relationship between a measurable area and a drive target area.
Figure 12:
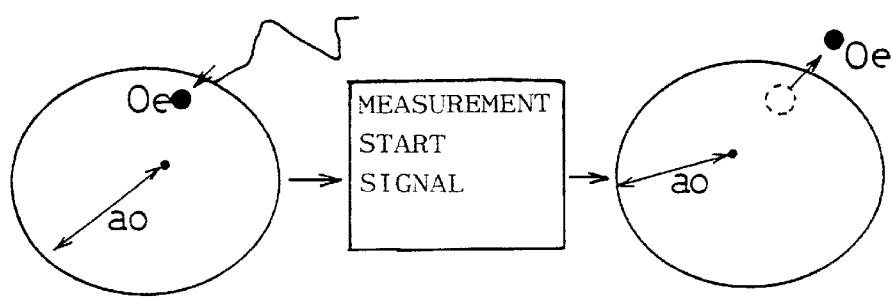
FIG. 12 is an explanatory drawing used to explain the problems found in a conventional ophthalmic instrument.

When the offset quantity $\Delta$ is equal to or less than $\Delta\bigcirc$, the control circuit 51 operates an incorporated timer (not shown) to measure the time elapsed since the offset quantity $\Delta$ has become equal to or less than $\Delta\bigcirc$, and also judges whether or not the offset quantity $\Delta$ has become equal to or less than a predetermined value $\Delta m$ (that is a value smaller by far than $\Delta\bigcirc$) within a predetermined time (e.g., 3 sec). That is, the present invention, as described later, does not send a measurement start signal immediately after the optical axis Oe of the object eye has been moved within the measurable area K, but drives a three-dimensional drive mechanism D for only a predetermined time so that the optical axis Oe of the object eye is moved within a range of $\Delta \leqq \Delta m$. That is, the control circuit 51 drives the three-dimensional drive mechanism D with the range of $\Delta \leqq \Delta m$ as a target. The reason for this is that in the case of $\Delta \leqq \Delta m$, even when the object eye I moves slightly, a danger of the optical axis Oe of the object eye moving out of the measurable area K is significantly reduced and therefore measured values can be obtained with reliability. The range of $\Delta \leqq \Delta m$ will hereinafter be referred to as a "drive target area L". The positional relationship between the drive target area L and the measurable area K is conceptually shown in FIG. 11.

Moreover, the control circuit 51 is constructed so that in a predetermined case, it sends a measurement start signal that instructs start of measurement toward an optical measuring section 101.

<OVERALL CONSTITUTION>

Figure 2:
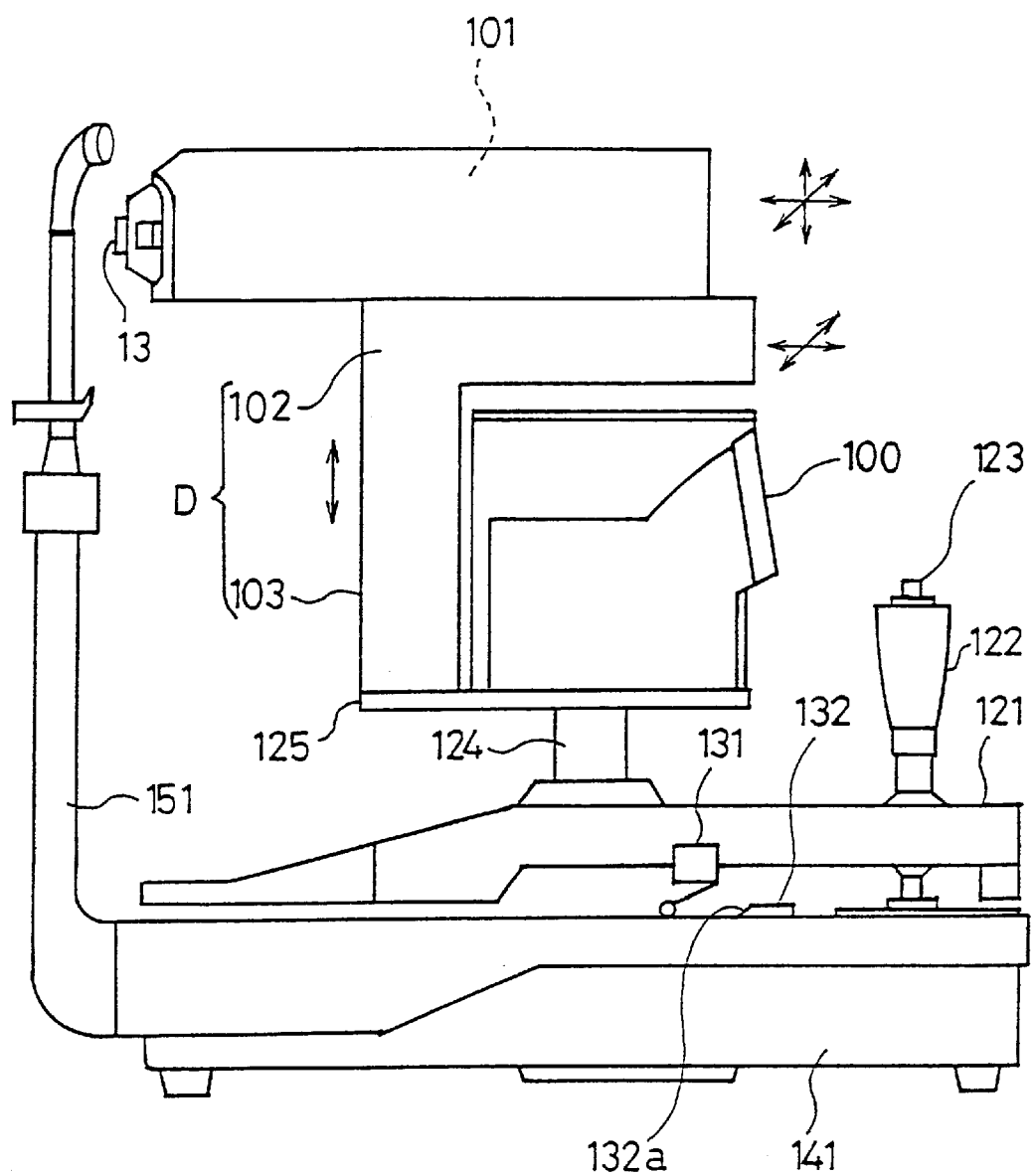
FIG. 2 is a side view of an ophthalmic instrument equipped with the optical system shown in FIG. 1.

Next, the overall constitution of the non-contact type tonometer, including the vertical drive unit 103 and the longitudinal-and-lateral drive unit 102, will be described in reference to FIG. 2.

In the figure, reference numeral 141 denotes a base incorporated with a power supply. A pedestal 121 is attached on the base 141 so that it is movable longitudinally and laterally. The rear portion of the pedestal 121 holds a joy stick 122 so that the joy stick 122 is freely tiltable in an arbitrary direction. By tilting this joy stick 122 longitudinally and laterally, the pedestal 121 is longitudinally and laterally moved on and along the base 141. Because this structure is well known in the prior art, a detailed description thereof will not be given. A manual measurement switch 123 is mounted on the upper end of the joy stick 122. This manual measurement switch 123 is used for starting measurement in a manual measurement mode to which description is not given.

A cam plate 132 with an inclined surface 132a at its front end portion is mounted on the upper surface of the aforementioned base 141, and a micro-switch 131 is attached to a side portion of the pedestal 121. This micro-switch 131 is turned on by the cam plate 132 when the pedestal 121 rearwardly moves, whereby the aforementioned solenoid (not shown) for driving the correcting lens 15 is driven and therefore the correcting lens 15 is moved into the optical axis O. A monitor mounting plate 125 is mounted at the center of the pedestal 121 with a support 124, and the monitor 100 is mounted on the monitor mounting plate 125.

Figure 1:
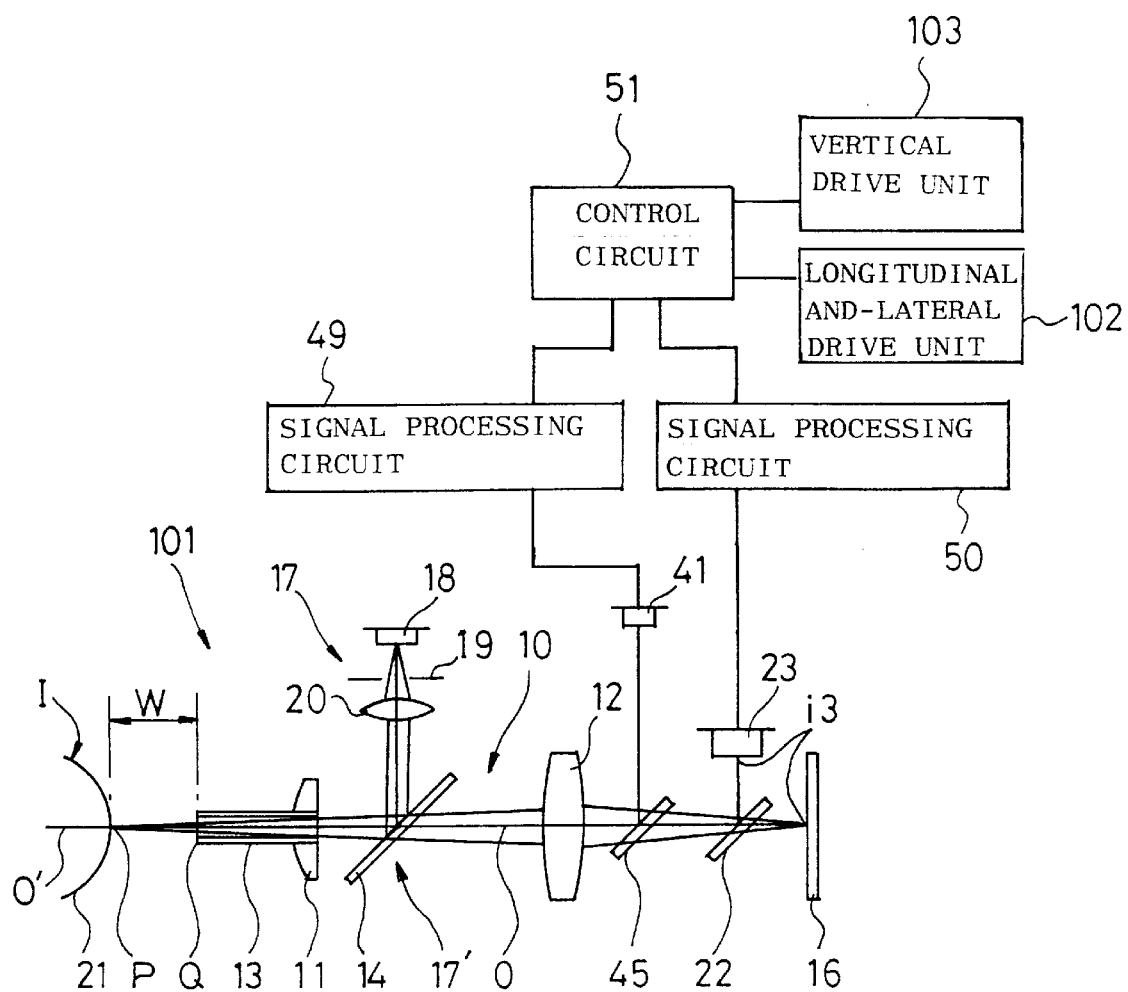
FIG. 1(B) is a side view showing the relationship between a control circuit and an optical system employing the inside of the spraying nozzle of FIG. 1(A) as an optical path.

The optical measuring section 101 housing the aforementioned optical systems of FIG. 1 is mounted above the front end portion of the monitor mounting plate 125 with the interposed three-dimensional drive mechanism D (drive means) composed of the aforementioned vertical drive unit 103 and longitudinal-and-lateral drive unit 102, so that the optical measuring section 101 is automatically movable in the X-, Y-, and Z-directions.

Next, the vertical drive unit 103 and the longitudinal-and-lateral drive unit 102 will be described in detail in reference to FIG. 3.

The vertical drive unit 103 includes a motor 104 and a support 105. The motor 104 and the support 105 are coupled by a pinion-rack mechanism (not shown) so that the support 105 is moved in the vertical direction (Y-direction) by the motor 104, The upper end of the support 105 is provided with a table 106.

Figure 4:
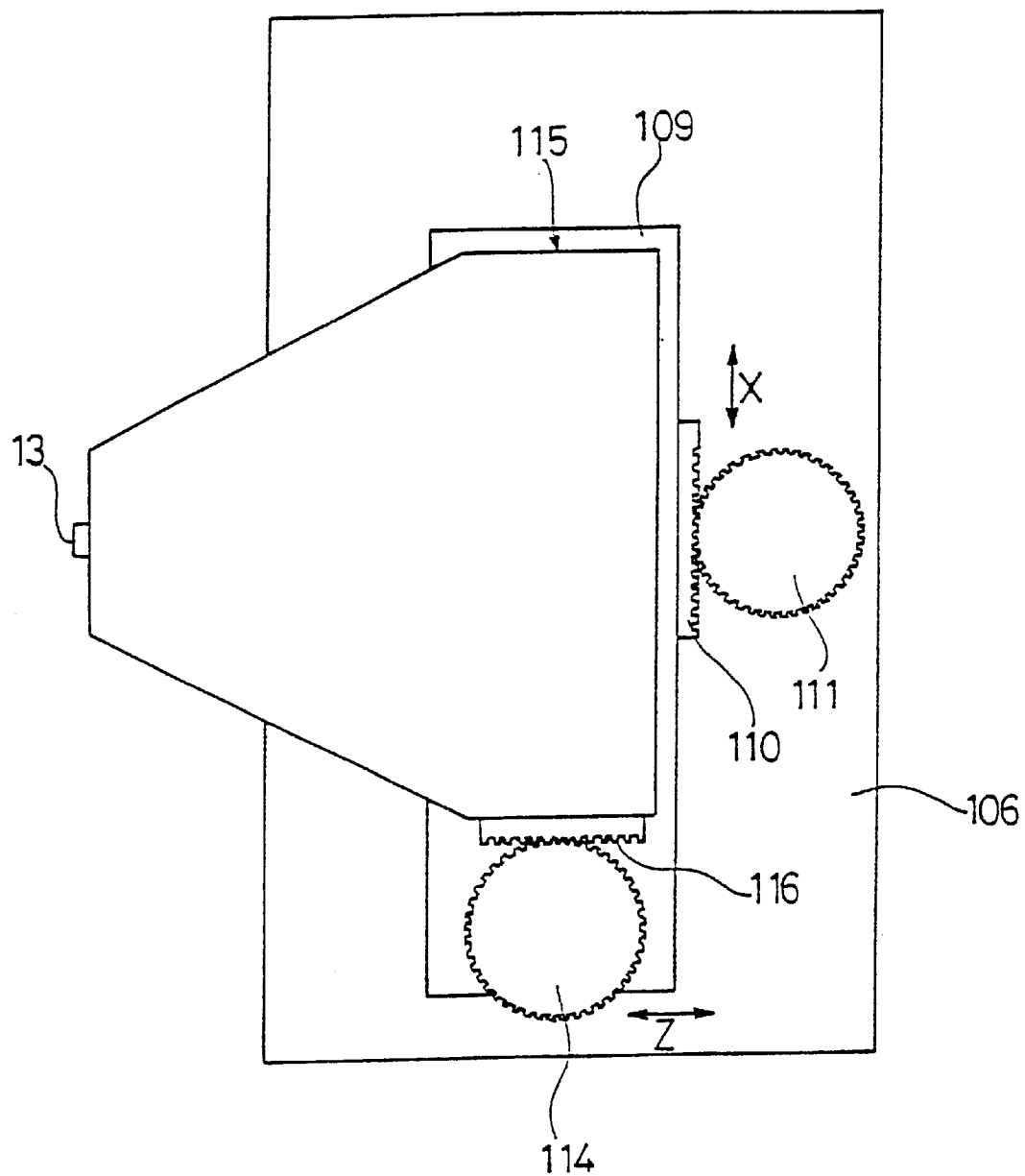
FIG. 4 is a plan view of the three-dimensional drive mechanism shown in FIG. 3.

The longitudinal-and-lateral drive unit 102 is equipped with a support 107 mounted on the table 106, a table 109 attached to the support 107 so that it is slidable in the X-direction, and a motor 108 mounted on the table 106. The rear end of the table 109 is provided with a rack 110, as shown in FIG. 4. This rack 110 meshes with a pinion 111 mounted on the output shaft of the motor 108. The longitudinal-and-lateral drive unit 102 is further equipped with a motor 112 mounted on the upper portion of the table 109 and a support 113. The upper portion of the support 113 is provided with a main body case 115 so that the case 115 can slide. In the case 115 the aforementioned optical measuring section 101 is housed. The side portion of the main body case 115 is provided with a rack 116 in a direction parallel to the Z-direction, as shown in FIG. 4. The rack 116 meshes with a pinion 114 mounted on the output shaft of the motor 112.

Based on the output of the control circuit 51, the motors 104, 108, and 112 of the vertical drive unit 103 and longitudinal-and-lateral drive unit 102 are rotated by required quantities, respectively. As a result, the optical measuring section 101 is moved in the Y-, X-, and Z-direction, whereby the alignment between the optical measuring section 101 and the object eye I is adjusted.

<OPERATION>

Next, the operation of the aforementioned ophthalmic instrument will be described.

The tester first pulls the pedestal 121 toward himself so that the micro-switch 131 is turned on by the cam plate 132 on the base 141. As a result, the correcting lens 15 is inserted into the optical axis O.

A reagent puts his chin on a chin receiver 151. Then, when the tester advances the pedestal 121 by pushing the joy stick 122 forward, the micro-switch 131 will be turned off. As a result, the correcting lens 15 is removed from the optical axis O. Then, based on the front eye portion image and the reticle image displayed on the monitor 100, the tester performs the rough alignment between the optical measuring section 101 and the object eye I by controlling the joy stick 122. When the rough alignment is completed, the light beams from the LEDs 26 and 27 will be reflected at the cornea 21 and incident on the light receiving elements 23 and 41. Then, the output signals from the light receiving elements 23 and 41 are input to the control circuit 51 through the signal processing circuits 49 and 50. The control circuit 51 transmits signals to the motor 104 of the vertical drive unit 103 and the motors 108 and 112 of the longitudinal-and-lateral drive unit 102 to move the optical measuring section 101 so that the optical axis Oe of the object eye is moved within the measurable area K.

As the result of the aforementioned operation, when the optical axis Oe of the object eye is moved within the measurable area K, the control circuit 51 further drives both the vertical drive unit 103 and the longitudinal-and-lateral drive unit 102 so that the optical axis Oe of the object eye is moved within the drive target area L. At the same time, in order to measure the time elapsed since the optical axis Oe of the object eye was moved within the measurable area K, the timer (not shown) in the control circuit 51 begins to operate. If the optical axis Oe of the object eye is moved within the drive target area L before the time measured by the timer exceeds a predetermined time (e.g., 3 sec), at this point the control circuit 51 transmits a measurement start signal to a compressed air generator (not shown). In response to the transmitted measurement start signal, this compressed air generator sprays compressed air over the object eye I through the spraying nozzle 13. The compressed air causes the cornea 21 of the object eye I to deform, so that the light quantity of the light beam, incident on the light receiving element 57 of the cornea-deformation detecting optical system 201, is changed. Based on the temporal change in the light quantity, the cornea-deformation detecting optical system 201 computes the intraocular tension by a known method. Since the measurement start signal is transmitted in the state in which the optical axis Oe of the object eye has been moved within the drive target area L, there is no possibility that the optical axis Oe of the object eye will be moved out of the measurable area K, when an air pulse is jetted after a predetermined time (e.g., 0.1 sec) has elapsed since the transmission of the measurement start signal, Therefore, it is believed that measured values are obtained with high reliability.

On the other hand, if the optical axis Oe of the object eye is not moved within the drive target area L after the time measured by the timer has exceeded a predetermined time (e.g., 3 sec), the control circuit 51 transmits a measurement start signal as long as the optical axis Oe of the object eye is within the measurable area K. The reason for this is that when the flicks of the object eye I are furious, it is extremely difficult to move the optical axis Oe of the object eye within the drive target area L, whereas measurement is possible as long as it is made within the measurable area K. However, in this case the reliability of the measured value is degraded in comparison with the case where measurement is started after the object eye axis Oe has been moved within the drive target area L. In such a case, as described above, there is a possibility that the measurement start signal will be transmitted in the state in which the optical axis Oe of the object eye is near the inside of the boundary of the measurable area K. In this case, there is a possibility that the optical axis Oe of the object eye will be moved out of the measurable area K when an air pulse is jetted.

Note that if the drive units 102 and 103 are driven in the order of Z-direction, Y-direction, and X-direction, then the offset of the optical measuring section 101 due to the influence of flicks can be minimized.

Incidentally, when measurement is carried out, the alignment offset quantity (offset quantity between the object eye axis Oe and the optical axis O) may be computed and displayed on the monitor 100. From this offset quantity, the tester can know the reliability of the measured value.

SECOND EMBODIMENT

Figure 5:
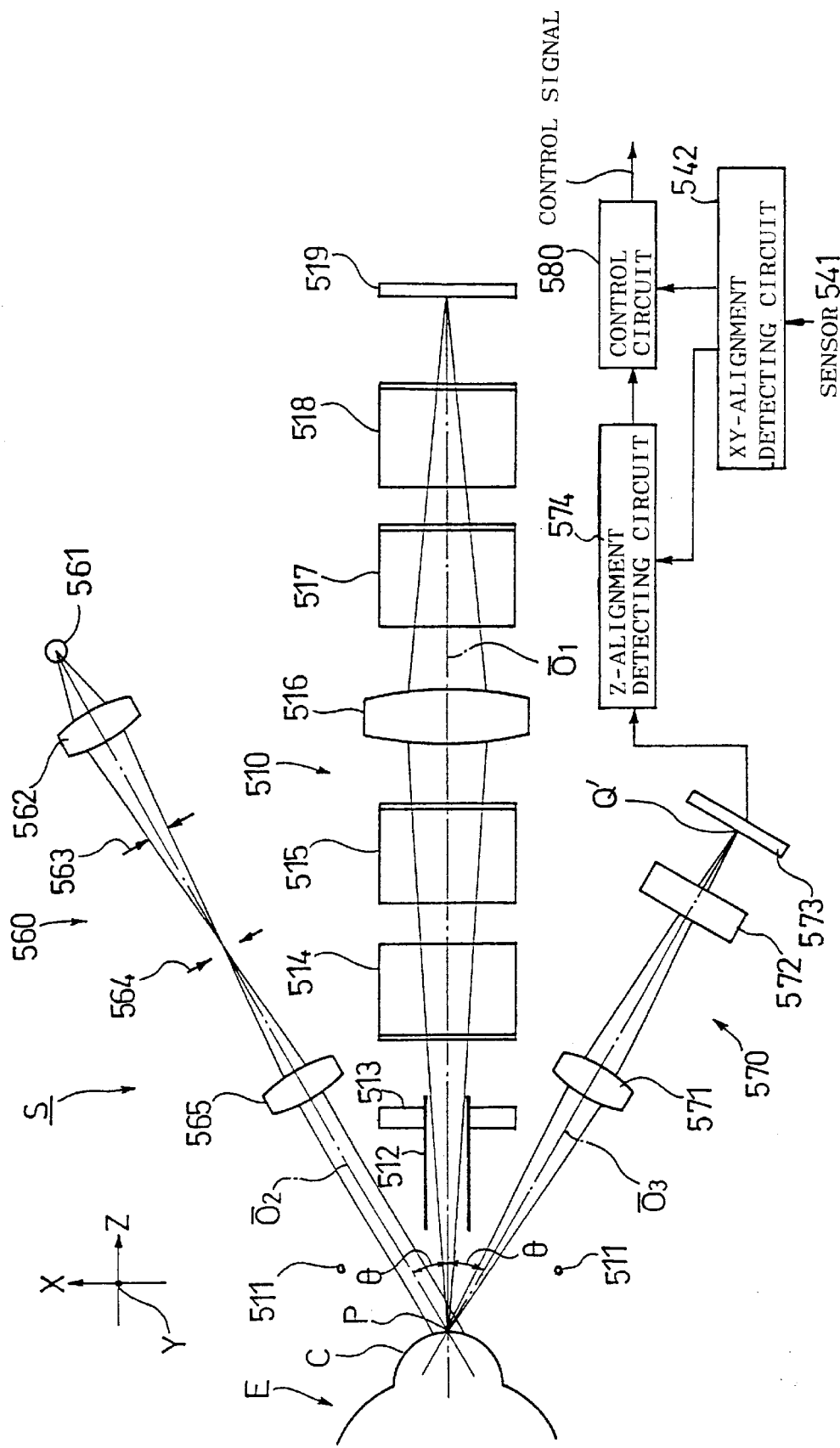
FIG. 5 is a plan view showing the plane distribution of main parts of the optical system of an ophthalmic instrument according to a second embodiment of the present invention.
Figure 6:
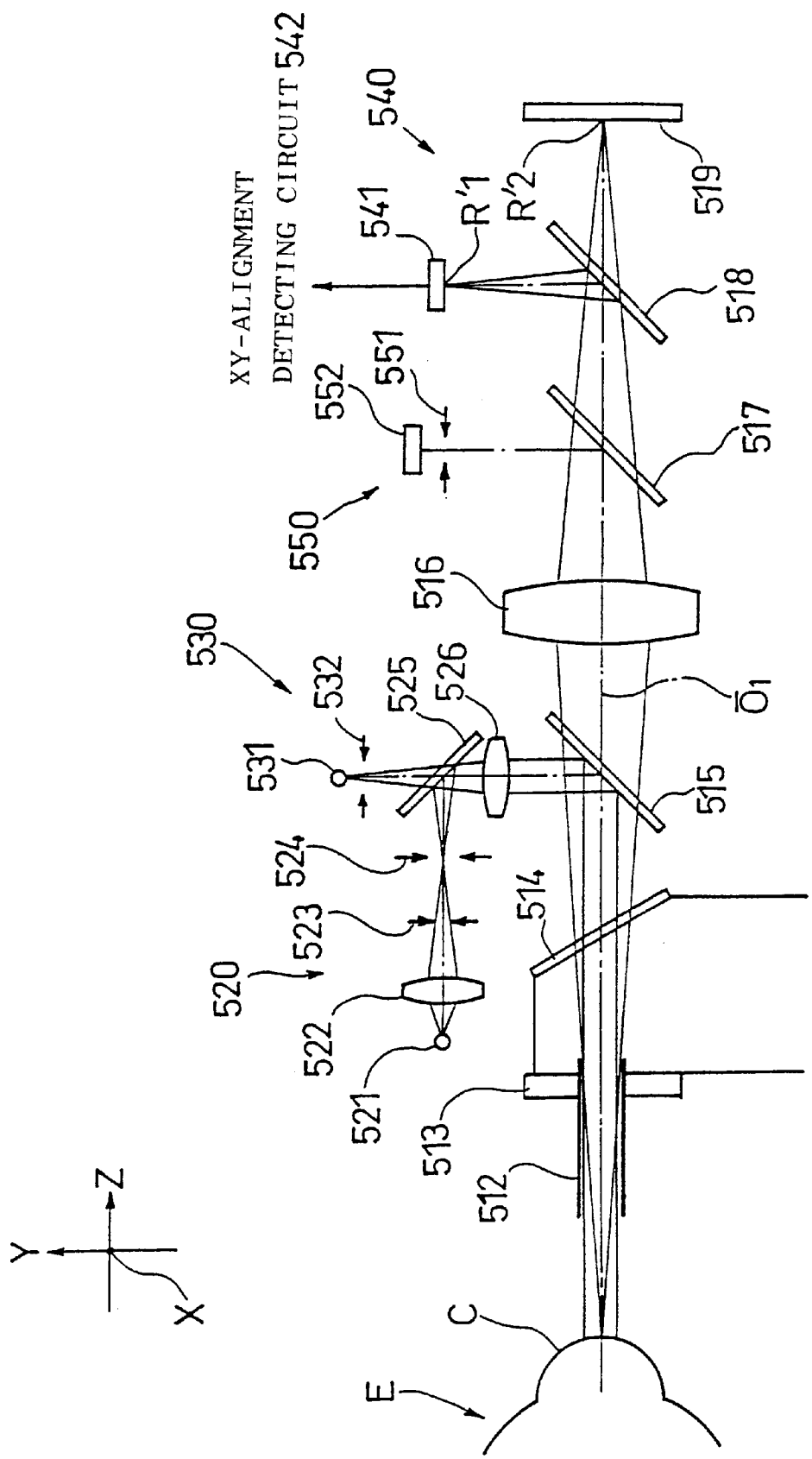
FIG. 6 is a side view showing the side distribution of main parts of the optical system of the ophthalmic instrument shown in FIG. 5.

In FIGS. 5 and 6, an ophthalmic instrument S according to a second embodiment of the present invention is equipped with a front eye portion observing system 510 for observing the front eye portion of an object eye E, an XY-alignment index light projecting optical system 520 for projecting an index light for XY-alignment detection and cornea deformation detection onto the cornea C of the object eye E from the front, and a fixation index light projecting optical system 530 for providing a fixation index light to the object eye E. The ophthalmic instrument S is further equipped with an XY-alignment detecting optical system 540 for receiving the reflected light of an XY-alignment index light reflected at the cornea C and detecting the positional relation in the XY-direction between the instrument S and the cornea C, a cornea-deformation detecting optical system 550 for receiving the reflected light of the XY-alignment index light reflected at the cornea C and detecting the deformation quantity of the cornea C, a Z-alignment index light projecting optical system 560 for projecting the Z-alignment index light onto the cornea C from an oblique direction, and a Z-alignment detecting optical system 570 for receiving the reflected light of the Z-alignment index light reflected at the cornea C from a direction symmetrical with respect to the optical axis of the front eye portion observing system 510 and detecting the positional relation in the Z-direction between the instrument S and the cornea C.

Figure 3:
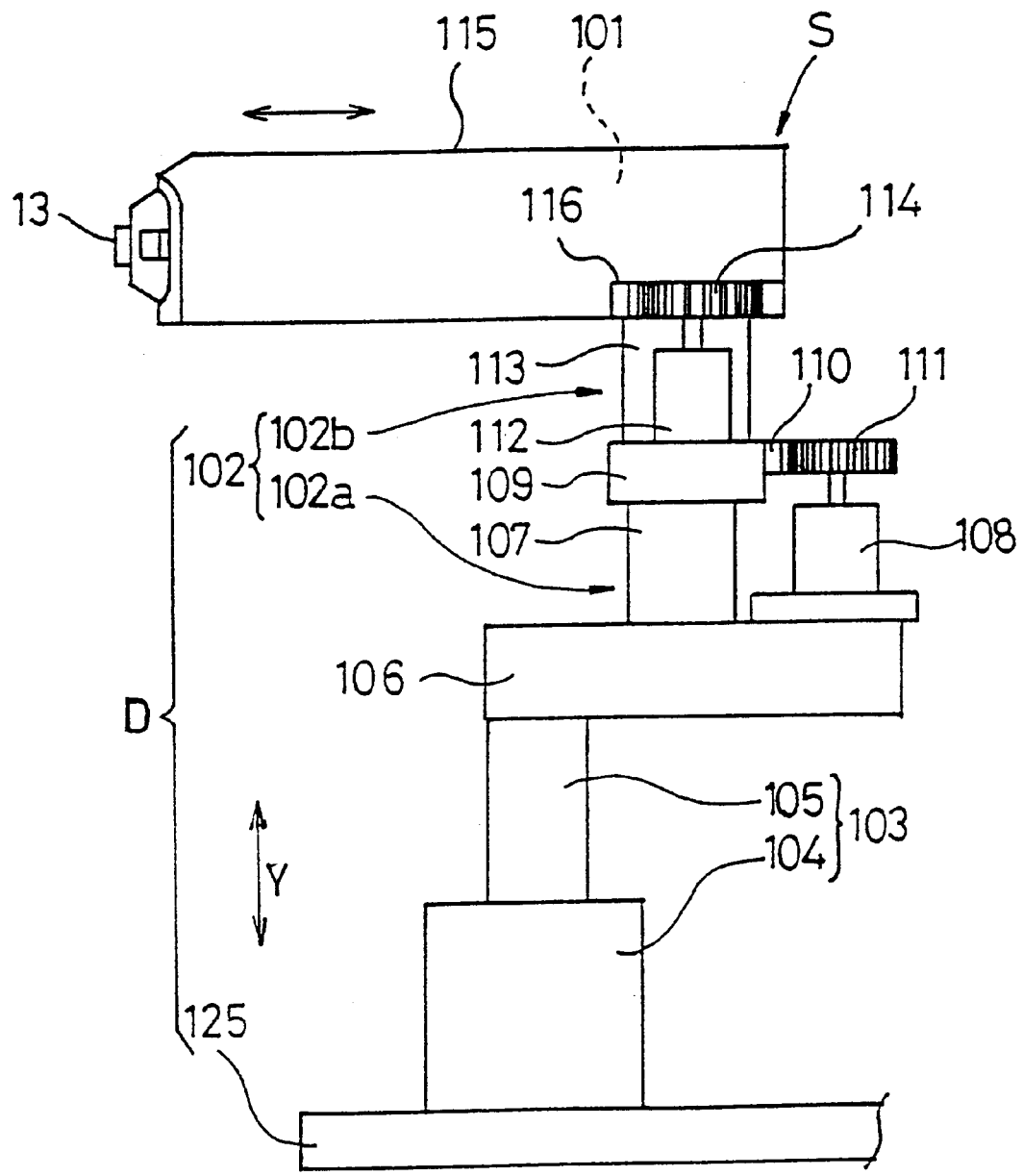
FIG. 3 is an explanatory drawing showing the three-dimensional drive mechanism of FIG. 2.

These optical systems 510, 520, 530, 540, 550, 560, and 570, as with the first embodiment, are provided within the main body case 115 shown in FIG. 3.

The front eye portion observing system 510 is equipped with a plurality of front eye portion illumination light sources 511 provided to the right and left of the object eye E for illuminating the front eye portion directly, an air spraying nozzle 512, a front eye portion window glass 513, a chamber window glass 514, a half mirror 515, an object lens 516, half mirrors 517 and 518, and a CCD camera 519. The optical axis of the front eye portion observing system 510 is represented by O1.

The image of the front eye portion of the object eye E, illuminated by the front eye portion illumination light sources 511, passes through the inside and outside of the air spraying nozzle 512 and is transmitted through the front eye portion window glass 513, chamber window glass 514, and half mirror 515. The transmitted image is focused by the objective lens 516 and transmitted through the half mirrors 517 and 518. Thus the image is fonned on the CCD camera 519.

The XY-alignment index light projecting optical system 520 has an XY-alignment light source 521 for emitting an infrared light, a condenser lens 522, an aperture diaphragm 523, a pinhole plate 524, a dichroic mirror 525, and a projection lens 526 arranged in an optical path so that it has its focal point at the position of the pinhole plate 524, The projecting system 520 further has the aforementioned half mirror 515, chamber window glass 514, and air spraying nozzle 512.

Figure 7:
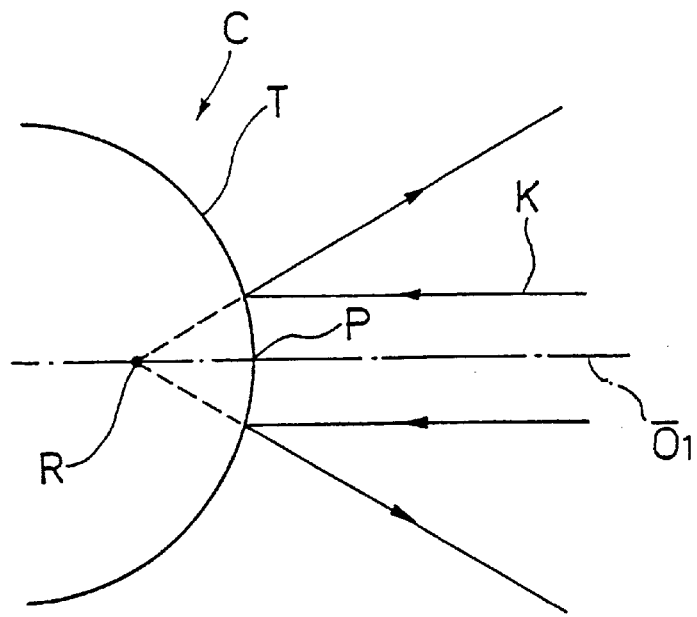
FIG. 7 is an explanatory drawing showing how a light beam for alignment that is irradiated from the front is reflected at the cornea of an object eye.

Infrared light emitted from the XY-alignment light source 521 passes through the aperture diaphragm 523 after being focused by the condenser lens 522, and is guided to the pinhole plate 524. Then, the light beam, passed through the pinhole plate 524, is reflected at the dichroic mirror 525 and is collimated by the projection lens 526. After the collimated light beam has been reflected by the first half mirror 515, it is transmitted through the chamber window glass 514 and passes through the inside of the air spraying nozzle 512, Finally, the light beam from the air spraying nozzle 512 forms an XY-alignment index light K, as shown in FIG. 7. In the figure, the XY-alignment index light K is reflected at the cornea surface T so that a bright spot image R is formed at the intermediate position between the vertex P of the cornea C and the center of curvature of the cornea C. Note that the aperture diaphragm 523 is provided at a position conjugate with the vertex P of the cornea C with respect to the projection lens 526.

The fixation index light projecting optical system 530 has a fixation index light source 531 for emitting visible light and a pinhole plate 532. The fixation index light projecting optical system 530 further has the aforementioned dichroic mirror 525, projection lens 526, half mirror 515, chamber window glass 514, and air spraying nozzle 512.

The fixation index light emitted from the fixation index light source 531 passes through the pinhole plate 532 and the dichroic mirror 525, and is collimated by the projection lens 526. After the collimated light beam has been reflected at the half mirror 515, it is transmitted through the chamber window glass 514. The transmitted light beam passes through the inside of the air spraying nozzle 512 and is guided to the object eye E. The reagent gazes steadily at the fixation index as a fixation target, whereby a line of sight is locked.

The XY-alignment detecting optical system 540 has the aforementioned air spraying nozzle 512, chamber window glass 514, half mirror 515, objective lens 516, and half mirrors 517 and 518. The XY-alignment detecting optical system 540 further has a sensor 541 and an XY-alignment detecting circuit 542.

The reflected light beam, projected on the cornea C by the XY-alignment index light projecting optical system 520 and reflected at the cornea surface T, passes through the inside of the nozzle 512 and is transmitted through the chamber window glass 514 and the half mirror 515. The transmitted light is focused by the objective lens 516 and partially transmitted through the half mirror 517, and then a portion of the transmitted light is reflected at the half mirror 518. The light beam, reflected at the half mirror 518, forms a bright spot image R'1 on the sensor 541 The sensor 541 is a light receiving sensor which can detect position, such as a PSD. The XY-alignment detecting circuit 542 computes the positional relation (XY-direction) between the instrument S and the cornea C by a known means on the basis of the output of the sensor 541, and outputs the result of computation to a Z-alignment detection correcting circuit 574 and a control circuit 580.

Figure 8:
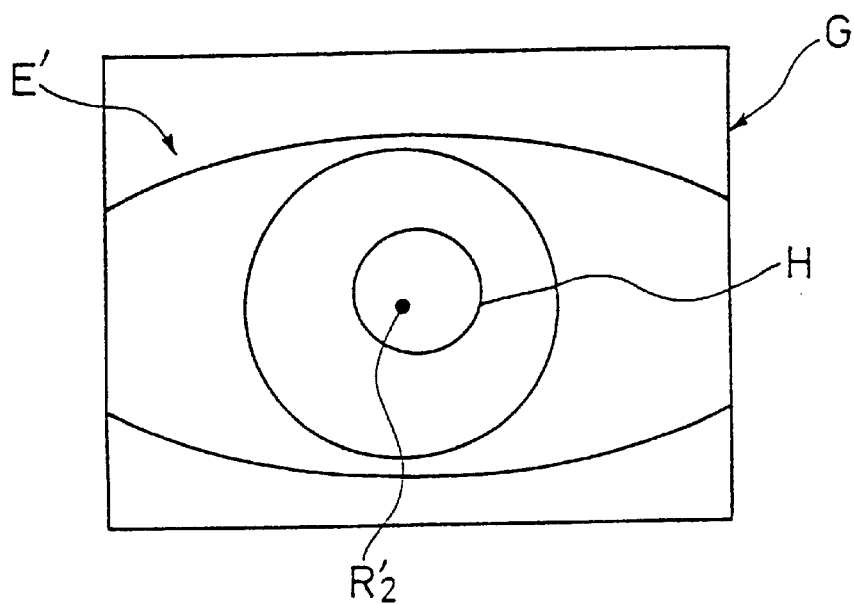
FIG. 8 is an explanatory drawing showing an image of the front eye portion of the object eye displayed on the screen of a monitor.

On the other hand, the light beam, reflected at the cornea C and transmitted through the half mirror 518, forms a bright spot image R'2 on the CCD camera 519. The CCD camera 519 outputs an image signal to a monitor. As shown in FIG. 8, a front eye portion image E' of the object eye E and the bright spot image R'2 of the XY-alignment index light are displayed on the screen G of the monitor. In FIG. 8, reference character H denotes an alignment auxiliary mark generated by image generating means (not shown).

Furthermore, the partial light beam reflected by the half mirror 17 is guided to the cornea-deformation detecting optical system 550. The guided light beam passes through a pinhole plate 551 and is guided to a sensor 552. The sensor 552 is a light receiving sensor which can detect a quantity of light, such as a photodiode.

The Z-alignment index light projecting optical system 560 has a Z-alignment light source 561 for emitting an infrared light, a condenser lens 562, an aperture diaphragm 563, a pinhole plate 564, and a projection lens 565 arranged in an optical path so that it has its focal point at the position of the pinhole plate 564. The optical axis of the Z-alignment index light projecting optical system 560 is represented by O2.

Figure 9:
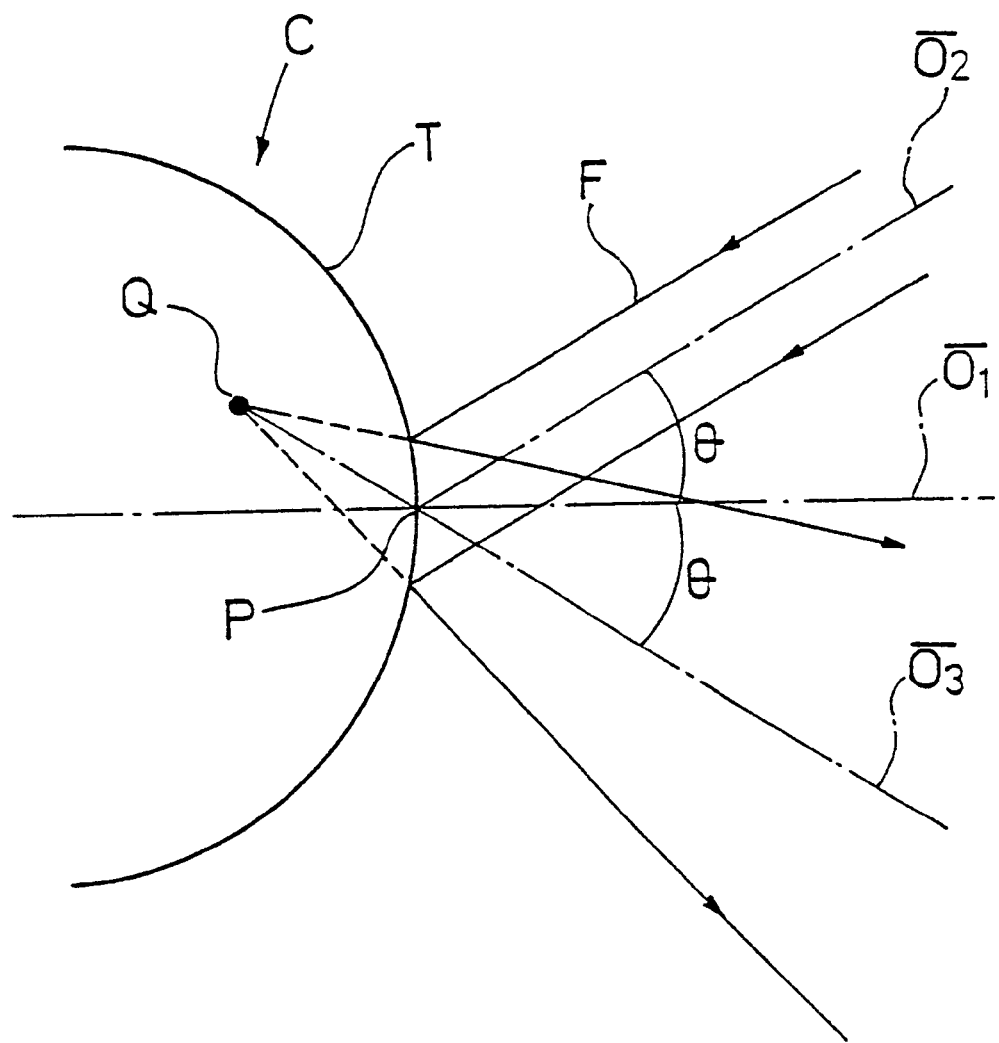
FIG. 9 is an explanatory drawing showing how a light beam for alignment, emitted to the cornea from an oblique direction, is reflected at the cornea.

An infrared light emitted from the Z-alignment light source 561 is focused by the condenser lens 562 and passes through the aperture diaphragm 563, and is guided to the pinhole plate 564. The light beam, transmitted through the pinhole plate 564, is collimated by the projection lens 565. The collimated light beam is guided to the cornea C. As shown in FIG. 9, the collimated light beam F is reflected at the cornea surface T so that it forms a bright spot image Q. Note that the aperture diaphragm 563 is provided at a position conjugate with the vertex P of the cornea C with respect to the projection lens 565.

The Z-alignment detecting optical system 570 has an image forming lens 571, a cylindrical lens 572 having power in the Y-direction, a sensor 573, and a Z-alignment detection correcting circuit 574. The optical axis of the Z-alignment detecting optical system 570 is represented by O3.

The index light, projected by the Z-alignment index light projecting optical system 560, is reflected at the cornea surface T. The reflected light beam forms a bright spot image Q' on the sensor 573 through the cylindrical lens 572 after being focused by the image forming lens 571. The sensor 573 is a light receiving sensor that can detect position, such as a line sensor or a PSD. Information from the sensor 573 is guided to the Z-alignment detection correcting circuit 574.

Note that within the XZ-plane, the bright spot image Q and the sensor 573 are in a relation of conjugate positions with respect to the image forming lens 571. Also, within the YZ-plane the vertex P of the cornea C and the sensor 573 are in a relation of conjugate positions with respect to the image forming lens 571 and the cylindrical lens 572. In other words, the sensor 573 and the aperture diaphragm 563 are in a conjugate relation (the magnification at this time is selected so that the image of the aperture diaphragm 563 becomes smaller than the size of the sensor 573). Therefore, even if the cornea C is shifted in the Y-direction, the reflected light beam at the cornea surface T will be efficiently incident on the sensor 573. Also, even if a slit light long in the Y-direction is projected, the efficiency will be reduced; however, the same effect can be obtained.

Incidentally, in the second embodiment, the light projecting and light receiving systems for detecting Z-alignment, as shown in FIG. 5, are the Z-alignment index light projecting optical system 560 and the Z-alignment detecting optical system 570, and they are provided one by one, respectively, In such constitution, in order to perform the Z-alignment accurately without the influence of XY-alignment offset, the XY-alignment information from the XY-alignment detecting circuit 542 is input to the Z-alignment detection correcting circuit 574.

Figure 10A:
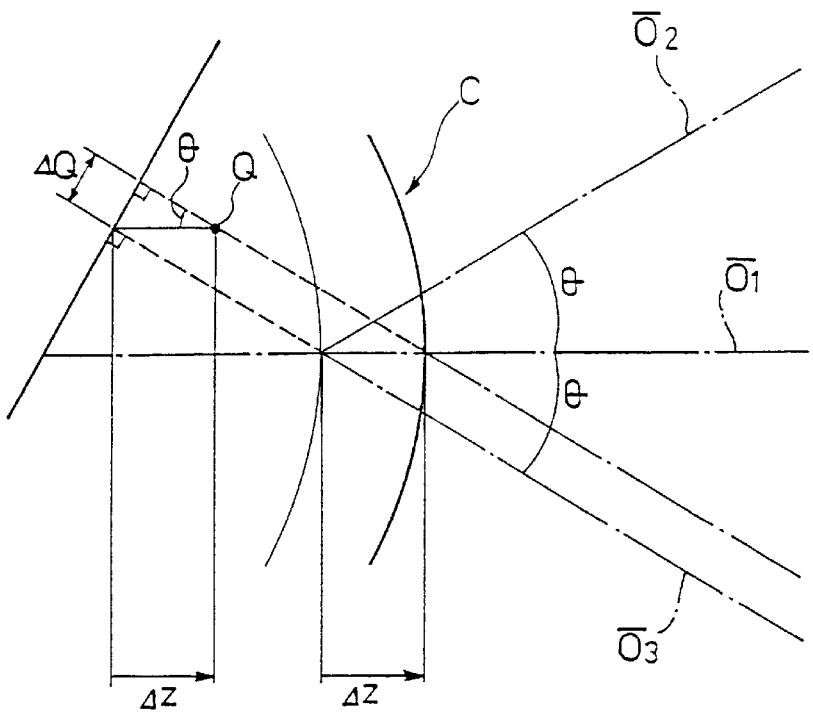
FIG. 10(A) is an explanatory drawing showing the relationship between the light incident on the cornea and the light reflected at the cornea when the cornea is shifted in the Z-direction.

More specifically, when the position of the cornea C is shifted by $\Delta Z$ in the Z-direction, as shown in FIG. 10(A), on the sensor 573 the position of the bright spot image Q' moves by $\Delta Z \times \sin\theta \times m$. In this equation, $\theta$ is the angle between the axis O1 and the axis O2 and the angle between the axis O2 and the axis O3, and m is the image forming magnification of the Z-alignment detecting optical system 570. If the cornea C is shifted only in the Z-direction, the offset quantity of the cornea C can be easily computed from the movement quantity of the bright spot Q' on the sensor 573.

Figure 10B:
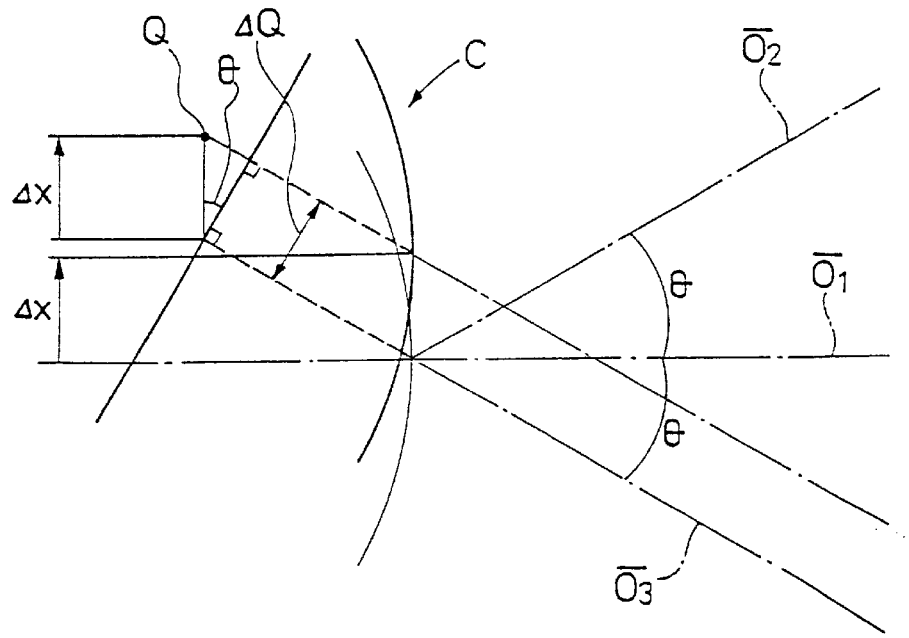
FIG. 10(B) is an explanatory drawing showing the relationship between the light incident on the cornea and the light reflected at the cornea when the cornea is shifted in the X-direction.

When the position of the cornea C is shifted by $\Delta X$ in the X-direction, as shown in FIG. 10(B), on the sensor 573 the position of the bright spot image Q' also moves by $\Delta X \times \cos\theta \times m$. Hence, when the position of the cornea C is shifted in both the Z-direction and the X-direction, the Z-alignment detection correcting circuit 574 computes the positional relation in the Z-direction between the instrument S and the cornea C (i.e., offset quantity $\Delta Z$) from both the offset quantity $\Delta Q'$ of the bright spot image Q' on the sensor 573 from a reference position and the offset quantity $\Delta X$ from the XY-alignment detecting circuit 542, based on the following Equation 1:

$$\Delta Z = (\Delta Q' - \Delta X \times \cos\theta \times m)/(\sin\theta \times m) \tag{1}$$

The computation result is output to the control circuit 580.

Next, the operation of the ophthalmic instrument in the second embodiment will be briefly described.

The tester first moves the instrument S in the X-direction and Y-direction manually so that the bright spot image R2' is moved within the alignment auxiliary mark H, while observing the front eye portion image E' with the monitor screen shown in FIG. 8. When the bright spot image R2' is moved within the alignment auxiliary mark H, then the reflected light beam of the index light, projected by the Z-alignment index light projecting optical system 560, is incident on the sensor 573. The control circuit 580 transmits signals to the motor 104 of the vertical drive unit 103 and the motors 108 and 112 of the longitudinal-and-lateral drive unit 102 to cause the optical measuring section 101 to move, whereby the optical axis Oe of the object eye is moved within the measurable area K. Since measurement is performed in the same manner as the first embodiment, a description thereof will not be given.

While the present invention has been described with reference to preferred embodiments thereof, the invention is not to be limited to the details given herein, but may be modified within the scope of the appended claims.

What is claimed is:

1. An ophthalmic instrument comprising:
    an optical measuring section for housing an optical system which measures characteristics of an object eye;
    an alignment detecting optical system for optically detecting an offset quantity in alignment between said optical measuring section and said object eye;
    drive means for moving said optical measuring section vertically, laterally, and longitudinally on the basis of said offset quantity detected by said alignment detecting optical system; and
    measurement start instructing means for transmitting a signal that instructs start of measurement to said optical measuring section when said alignment detecting optical system detects that said object eye has been moved within a measurable area;
    wherein prior to operation of said measurement start instructing means, said drive means continues to move said optical measuring section for only a predetermined time so that said object eye is moved within a drive target area smaller than said measurable area and also included in said measurable area.

2. The ophthalmic instrument as set forth in claim 1, wherein said offset quantity in the alignment is computed when measurement is started by said measurement start instructing means, and the computed offset quantity is informed.

3. The ophthalmic instrument as set forth in claim 1, wherein, when said object eye is moved within said drive target area before said predetermined time elapses, said measurement start signal is output in order to start measurement.

4. The ophthalmic instrument as set forth in claim 1, wherein, when said object eye is not moved within said drive target area after said predetermined time elapses, said measurement start signal is output in order to start measurement if said object eye is within said measurable area.

* * * * *